(12) United States Patent
Williams et al.

(10) Patent No.: US 9,918,049 B2
(45) Date of Patent: *Mar. 13, 2018

(54) RECALL DEVICE

(71) Applicant: Microsoft Technology Licensing, LLC, Redmond, WA (US)

(72) Inventors: Lyndsay Williams, Cambridge (GB); Kenneth Robert Woodberry, Cambridge (GB); Kevin Michael Schofield, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/132,598

(22) Filed: Apr. 19, 2016

(65) Prior Publication Data
US 2016/0295175 A1  Oct. 6, 2016

Related U.S. Application Data

(63) Continuation of application No. 14/514,964, filed on Oct. 15, 2014, now Pat. No. 9,344,688, which is a
(Continued)

(51) Int. Cl.
  *H04N 5/225* (2006.01)
  *H04N 7/18* (2006.01)
  (Continued)

(52) U.S. Cl.
  CPC ............ *H04N 7/188* (2013.01); *A61B 5/1117* (2013.01); *A61B 5/1123* (2013.01); *G01S 19/34* (2013.01);
(Continued)

(58) Field of Classification Search
  CPC ..... H04N 5/225; H04N 5/232; H04N 5/23248
  See application file for complete search history.

(56) References Cited

U.S. PATENT DOCUMENTS 4,009,943 A   3/1977 Horimoto
4,461,553 A   7/1984 Doerr et al.
(Continued)

FOREIGN PATENT DOCUMENTS

EP   0846440   6/1998
GB   2250156   5/1992
(Continued)

OTHER PUBLICATIONS

"Notice of Allowance Issued in European Patent Application No. 05101439.7", dated Jul. 14, 2009, 4 Pages.
(Continued)

*Primary Examiner* — Eric D. Bertram
(74) *Attorney, Agent, or Firm* — Christopher J. Volkmann; Kelly, Holt & Christenson, PLLC

(57) ABSTRACT

A small wearable recall device is provided to capture images triggered by a combination of a detection of a capture condition (e.g., changes in motion, temperature or light level) followed by a relatively stable period, as detected by an accelerometer. By triggering on the combination of a detected capture condition followed by a detected stability condition, a clearer image of the environment of an interesting event is expected to be captured. The small size of the recall device makes it possible to integrate it into common portable consumer products, such as MP3 players, purses, clothing, hats, backpacks, necklaces, collars, and other human-wearable products.

18 Claims, 6 Drawing Sheets

Related U.S. Application Data continuation of application No. 10/790,602, filed on Mar. 1, 2004, now Pat. No. 8,886,298.

(51) Int. Cl.

| | |
|---|---|
| H04N 5/232 | (2006.01) |
| A61B 5/11 | (2006.01) |
| G01S 19/34 | (2010.01) |
| G08B 13/196 | (2006.01) |
| G08B 15/00 | (2006.01) |
| H04L 29/08 | (2006.01) |
| H04L 29/06 | (2006.01) |
| H04L 29/12 | (2006.01) |
| G06F 11/20 | (2006.01) |
| G06F 21/62 | (2013.01) |
| G07F 17/16 | (2006.01) |
| G06Q 20/10 | (2012.01) |
| G06Q 20/12 | (2012.01) |
| G06Q 20/38 | (2012.01) |
| G06Q 20/40 | (2012.01) |
| G06Q 20/42 | (2012.01) |
| G06Q 30/02 | (2012.01) |
| H01M 16/00 | (2006.01) |
| H04B 1/04 | (2006.01) |
| H04B 1/40 | (2015.01) |
| H04B 7/06 | (2006.01) |
| H04B 7/08 | (2006.01) |
| H04J 13/12 | (2011.01) |
| H04L 1/00 | (2006.01) |
| H04L 1/06 | (2006.01) |
| H04L 1/08 | (2006.01) |
| H04L 1/18 | (2006.01) |
| H04L 5/00 | (2006.01) |
| H04L 9/32 | (2006.01) |
| H04L 12/12 | (2006.01) |
| H04L 12/28 | (2006.01) |
| H04L 12/40 | (2006.01) |
| H04L 12/44 | (2006.01) |
| H04L 12/54 | (2013.01) |
| H04L 12/64 | (2006.01) |
| H04L 27/26 | (2006.01) |
| H04M 1/02 | (2006.01) |
| H04M 1/253 | (2006.01) |
| H04M 3/22 | (2006.01) |
| H04M 3/42 | (2006.01) |
| H04M 7/00 | (2006.01) |
| H04N 1/00 | (2006.01) |
| H04N 7/01 | (2006.01) |
| H04N 7/08 | (2006.01) |
| H04N 7/14 | (2006.01) |
| H04N 21/61 | (2011.01) |
| H04N 21/647 | (2011.01) |
| H04W 24/00 | (2009.01) |
| H04W 28/14 | (2009.01) |
| H04W 52/14 | (2009.01) |
| H04W 52/24 | (2009.01) |
| H04W 52/46 | (2009.01) |
| H04W 52/48 | (2009.01) |
| H04W 74/02 | (2009.01) |
| H04W 76/02 | (2009.01) |
| G06Q 30/06 | (2012.01) |
| H04L 12/24 | (2006.01) |
| H04L 12/801 | (2013.01) |
| H04L 12/815 | (2013.01) |
| G06Q 50/18 | (2012.01) |
| H04L 12/863 | (2013.01) |
| H04L 12/851 | (2013.01) |
| H04L 12/841 | (2013.01) |
| H04N 5/77 | (2006.01) |
| H04N 1/21 | (2006.01) |
| G06F 11/16 | (2006.01) |
| H04B 7/155 | (2006.01) |
| H04N 1/32 | (2006.01) |
| H04W 8/00 | (2009.01) |
| H04W 8/04 | (2009.01) |
| H04W 48/16 | (2009.01) |
| H04W 52/22 | (2009.01) |
| H04W 72/08 | (2009.01) |
| H04W 80/10 | (2009.01) |
| H04W 84/12 | (2009.01) |
| H04W 88/16 | (2009.01) |

(52) U.S. Cl.
CPC ...... *G06F 11/2005* (2013.01); *G06F 11/2007* (2013.01); *G06F 21/6218* (2013.01); *G06F 21/6245* (2013.01); *G06Q 20/10* (2013.01); *G06Q 20/1235* (2013.01); *G06Q 20/385* (2013.01); *G06Q 20/401* (2013.01); *G06Q 20/425* (2013.01); *G06Q 30/0277* (2013.01); *G06Q 30/0609* (2013.01); *G06Q 50/188* (2013.01); *G07F 17/16* (2013.01); *G08B 13/19621* (2013.01); *G08B 13/19628* (2013.01); *G08B 13/19695* (2013.01); *G08B 15/004* (2013.01); *H01M 16/006* (2013.01); *H04B 1/0483* (2013.01); *H04B 1/40* (2013.01); *H04B 7/0604* (2013.01); *H04B 7/084* (2013.01); *H04B 7/15535* (2013.01); *H04J 13/12* (2013.01); *H04L 1/0041* (2013.01); *H04L 1/0045* (2013.01); *H04L 1/0066* (2013.01); *H04L 1/0069* (2013.01); *H04L 1/0071* (2013.01); *H04L 1/06* (2013.01); *H04L 1/08* (2013.01); *H04L 1/1819* (2013.01); *H04L 1/1841* (2013.01); *H04L 1/1848* (2013.01); *H04L 5/0023* (2013.01); *H04L 5/0042* (2013.01); *H04L 5/0044* (2013.01); *H04L 5/0083* (2013.01); *H04L 9/32* (2013.01); *H04L 12/12* (2013.01); *H04L 12/2803* (2013.01); *H04L 12/2809* (2013.01); *H04L 12/2856* (2013.01); *H04L 12/2874* (2013.01); *H04L 12/40078* (2013.01); *H04L 12/40195* (2013.01); *H04L 12/44* (2013.01); *H04L 12/56* (2013.01); *H04L 12/6418* (2013.01); *H04L 27/2602* (2013.01); *H04L 29/06027* (2013.01); *H04L 29/12113* (2013.01); *H04L 41/12* (2013.01); *H04L 47/10* (2013.01); *H04L 47/14* (2013.01); *H04L 47/22* (2013.01); *H04L 47/2441* (2013.01); *H04L 47/28* (2013.01); *H04L 47/34* (2013.01); *H04L 47/50* (2013.01); *H04L 47/621* (2013.01); *H04L 61/1541* (2013.01); *H04L 63/0428* (2013.01); *H04L 63/065* (2013.01); *H04L 63/08* (2013.01); *H04L 63/0807* (2013.01); *H04L 63/102* (2013.01); *H04L 63/1441* (2013.01); *H04L 65/103* (2013.01); *H04L 65/104* (2013.01); *H04L 65/1043* (2013.01); *H04L 67/12* (2013.01); *H04L 67/14* (2013.01); *H04L 67/16* (2013.01); *H04L 67/306* (2013.01); *H04L 69/16* (2013.01); *H04L 69/168* (2013.01); *H04L 69/329* (2013.01); *H04M 1/0214* (2013.01); *H04M 1/2535* (2013.01); *H04M 3/22* (2013.01); *H04M 3/42* (2013.01); *H04M*

7/0057 (2013.01); *H04M 7/0069* (2013.01); *H04N 1/00127* (2013.01); *H04N 1/00132* (2013.01); *H04N 1/00137* (2013.01); *H04N 1/00148* (2013.01); *H04N 1/00342* (2013.01); *H04N 1/2133* (2013.01); *H04N 5/23248* (2013.01); *H04N 5/772* (2013.01); *H04N 7/0112* (2013.01); *H04N 7/08* (2013.01); *H04N 7/148* (2013.01); *H04N 21/6125* (2013.01); *H04N 21/64738* (2013.01); *H04N 21/64784* (2013.01); *H04W 24/00* (2013.01); *H04W 28/14* (2013.01); *H04W 52/143* (2013.01); *H04W 52/24* (2013.01); *H04W 52/245* (2013.01); *H04W 52/46* (2013.01); *H04W 52/48* (2013.01); *H04W 74/02* (2013.01); *H04W 76/02* (2013.01); *A61B 2562/0219* (2013.01); *G03B 2217/005* (2013.01); *G06F 11/1625* (2013.01); *G06F 2221/2101* (2013.01); *G06F 2221/2141* (2013.01); *G06F 2221/2149* (2013.01); *H01M 2250/30* (2013.01); *H04B 7/0894* (2013.01); *H04B 7/15507* (2013.01); *H04L 1/1845* (2013.01); *H04L 65/80* (2013.01); *H04L 69/324* (2013.01); *H04L 69/326* (2013.01); *H04L 2001/0096* (2013.01); *H04L 2012/40241* (2013.01); *H04L 2012/40273* (2013.01); *H04L 2012/6462* (2013.01); *H04L 2209/127* (2013.01); *H04M 1/0225* (2013.01); *H04M 1/0235* (2013.01); *H04M 3/42102* (2013.01); *H04N 1/32128* (2013.01); *H04N 2201/0017* (2013.01); *H04N 2201/0084* (2013.01); *H04N 2201/3205* (2013.01); *H04N 2201/3226* (2013.01); *H04W 8/005* (2013.01); *H04W 8/04* (2013.01); *H04W 48/16* (2013.01); *H04W 52/225* (2013.01); *H04W 52/241* (2013.01); *H04W 52/242* (2013.01); *H04W 72/08* (2013.01); *H04W 80/10* (2013.01); *H04W 84/12* (2013.01); *H04W 88/16* (2013.01); *Y02B 90/18* (2013.01); *Y10S 707/99933* (2013.01); *Y10S 707/99936* (2013.01); *Y10S 707/99939* (2013.01)

(56) References Cited

U.S. PATENT DOCUMENTS

| | | | |
|---|---|---|---|
| 4,901,096 A | 2/1990 | Lemelson | |
| 5,712,679 A | 1/1998 | Coles | |
| 5,790,490 A | 8/1998 | Satoh et al. | |
| 5,978,603 A | 11/1999 | Shiozaki et al. | |
| 6,181,373 B1 | 1/2001 | Coles | |
| 6,301,440 B1 | 10/2001 | Bolle et al. | |
| 6,317,114 B1 | 11/2001 | Abali et al. | |
| 6,542,824 B1 | 4/2003 | Berstis | |
| 6,558,050 B1 * | 5/2003 | Ishibashi | G08B 15/004 348/158 |
| 6,563,532 B1 | 5/2003 | Strub et al. | |
| 6,696,943 B1 | 2/2004 | Elrod et al. | |
| 6,825,875 B1 | 11/2004 | Strub et al. | |
| 8,886,298 B2 | 11/2014 | Williams et al. | |
| 9,344,688 B2 | 5/2016 | Williams et al. | |
| 2001/0043277 A1 | 11/2001 | Tanaka et al. | |
| 2002/0109600 A1 | 8/2002 | Mault et al. | |
| 2002/0159770 A1 | 10/2002 | Moultrie | |
| 2003/0025798 A1 | 2/2003 | Grosvenor et al. | |
| 2003/0030465 A1 | 2/2003 | Robins et al. | |
| 2003/0217240 A1 | 11/2003 | Satomi et al. | |
| 2004/0088328 A1 | 5/2004 | Cook et al. | |
| 2004/0133600 A1 | 7/2004 | Homer | |
| 2004/0156616 A1 | 8/2004 | Strub et al. | |
| 2004/0186854 A1 | 9/2004 | Choi | |
| 2004/0208496 A1 | 10/2004 | Pilu | |
| 2004/0215663 A1 | 10/2004 | Liu et al. | |
| 2004/0267812 A1 | 12/2004 | Harris et al. | |
| 2005/0012830 A1 | 1/2005 | Pilu | |
| 2005/0018073 A1 | 1/2005 | Pilu | |
| 2005/0062841 A1 | 3/2005 | Rivera-Cintron | |
| 2005/0160113 A1 | 7/2005 | Sipusic et al. | |
| 2005/0165843 A1 | 7/2005 | Capps et al. | |
| 2005/0193017 A1 | 9/2005 | Kim | |
| 2015/0086177 A1 | 3/2015 | Williams et al. | |

FOREIGN PATENT DOCUMENTS

| | | |
|---|---|---|
| JP | S64-86122 A | 3/1989 |
| JP | 02-280478 | 11/1990 |
| JP | 03276144 | 6/1991 |
| JP | 4504016 | 7/1992 |
| JP | 08-205133 | 8/1996 |
| JP | 11-317904 | 11/1999 |
| JP | 2000-196934 | 7/2000 |
| JP | 2000-285221 | 10/2000 |
| JP | 2001-036800 | 2/2001 |
| JP | 2001-166351 | 6/2001 |
| JP | 2001-309211 | 11/2001 |
| JP | 2002-51156 | 2/2002 |
| JP | 2002-150273 | 5/2002 |
| JP | 2002-218382 | 8/2002 |
| JP | 2002-247434 | 8/2002 |
| JP | 2002-131796 | 9/2002 |
| JP | 2003-032668 | 1/2003 |
| JP | 2003-230090 | 8/2003 |
| JP | 2003-234953 | 8/2003 |
| RU | 2089932 | 9/1997 |
| WO | 02/47465 | 6/2002 |

OTHER PUBLICATIONS

"Office Action Issued in European Patent Application No. 05101439.7", dated Nov. 27, 2008, 4 Pages.

"Notice of Allowance Issued in Korean Patent Application No. 10-2005-0017429", dated Feb. 21, 2014, 2 Pages. (W/o English Translation).

"Notice of Allowance Issued in Japanese Patent Application No. 2005-047233", dated Jun. 4, 2010, 1 Page.

"Notice of Allowance Issued in Chinese Patent Application No. 200510052618.3", dated Nov. 14, 2008, 2 Pages.

"Notice of Allowance Issued in Canadian Patent Application No. 2498703", dated Feb. 23, 2010, 1 Page.

"Notice of Allowance Issued in Mexican Patent Application No. PA/a/2005/002371", dated Aug. 31, 2009, 1 Page. (W/o English Translation).

Korean Notice of Final Rejection dated Apr. 17, 2012 for Application No. 10-2005-0017429, filed Mar. 2, 2005, 4 pages.

Mexican Office Action dated Jun. 24, 2008 for Application No. PA/a/2005/002371, 2 pages.

Russian Office Action dated Apr. 1, 2009 for Application No. 2005105513, with English Translation, 4 pages.

Australian Office Action Communication dated Feb. 2, 2009 for Application No. 2005201008, 2 pages.

Chinese First Office Action dated Dec. 21, 2007 for Application No. 200510052618.3 with English Translation, 22 pages.

Chinese Second Office Action dated Jun. 6, 2008 for Application No. 200510052618.3 with English Translation, 25 pages.

Korean Notice of Rejection dated Aug. 25, 2011 for Application No. 10-2005-0017429, 4 pages.

Notice from David Kappos dated Jan. 26, 2010, 1 page.

Japanese Notice of Rejection dated Nov. 10, 2009 for Application No. 2005-047233 with English Translation, 9 pages.

Japanese Final Rejection dated Apr. 1, 2010 for Application No. 2005-047233 with English Translation, 14 pages.

Healey, Jennifer, and Rosalind W. Picard. "StartleCam: a cybernetic wearable camera." In Wearable Computers, 1998. Digest of Papers. Second International Symposium on, pp. 42-49. IEEE, 1998.

(56) References Cited

OTHER PUBLICATIONS

EPO Communication with European Search Report for European Patent Application No. 05101439.07-1248, completed on Jun. 14, 2005, European Patent Office. 3 pages.
Clarkson, Brian Patrick. Life patterns: structure from wearable sensors. Diss. Massachusetts Institute of Technology, 2002. 130 pages.
Healey, Jennifer; "The StartleCam System", Feb. 1999, 3 pages http://www-white.media.mit.edu/tech-reports/TR-468/node3.html.
de Bruijn, Oscar, and Robert Spence. "Rapid serial visual presentation: a space-time trade-off in information presentation." Advanced visual interfaces. 2000. 4 pages.
Aizawa, Kiyoharu, Kenichiro Ishijima, and Makoto Shiina. "Summarizing wearable video." Image Processing, 2001. Proceedings. 2001 International Conference on. vol. 3. IEEE, 2001. 4 pages.
Prosecution History for U.S. Appl. No. 10/790,602 including: Issue Notification dated Oct. 22, 2014, Response to Notice to File Corrected Application Papers dated Sep. 24, 2014, Notice to File Corrected Application Papers dated Sep. 4, 2014, Notice of Allowance dated Jul. 11, 2014, Response After Final Action dated Jul. 3, 2014, Final Office Action dated Jan. 29, 2014, Amendment dated Nov. 20, 2013, Applicant Initiated Interview Summary dated Nov. 12, 2013, Part 1 of 4.
Prosecution History for U.S. Appl. No. 10/790,602 including: Non-Final Office Action dated Aug. 13, 2013, Amendment with RCE dated Mar. 28, 2012, Final Office Action dated Jan. 19, 2012, Amendment dated Nov. 9, 2011, Non-Final Office Action dated Jul. 29, 2011, Amendment with RCE dated May 24, 2011, Final Office Action dated Mar. 3, 2011, Amendment dated Dec. 14, 2010, Non-Final Office Action dated Sep. 20, 2010, Amendment with RCE dated May 5, 2010, Part 2 of 4.
Prosecution History for U.S. Appl. No. 10/790,602 including: Final Office Action dated Jan. 5, 2010, Amendment dated Sep. 8, 2009, Non-Final Office Action dated Jun. 8, 2009, Amendment with RCE dated May 26, 2009, Final Office Action dated Nov. 26, 2008, Amendment dated Aug. 13, 2008, Non-Final Office Action dated May 13, 2008, Amendment with RCE dated Oct. 23, 2007, Advisory Action dated Sep. 20, 2007, Response After Final Action dated Aug. 23, 2007, Final Office Action dated May 23, 2007, Part 3 of 4.
Prosecution History for U.S. Appl. No. 10/790,602 including: Amendment dated Mar. 21, 2007, Office Action dated Dec. 21, 2006, Withdrawal of Previously Sent Notice dated Jun. 6, 2005, Petition Decision dated May 31, 2005, Petition for Review by the Office of Petitions dated May 6, 2005, Response to Notice to File Corrected Application Papers dated May 2, 2005, Notice of Abandonment dated Feb. 11, 2005, Notice to File Corrected Application Papers dated May 24, 2004, Application and Drawings filed Mar. 1, 2004, Part 4 of 4. 386 pages.
Office Action dated Apr. 29, 2009 in U.S. Appl. No. 11/490,540, 55 pages.
Prosecution History for U.S. Appl. No. 14/514,964 including: Notice of Allowance dated Jan. 20, 2016, Amendment After Final dated Jan. 7, 2016, Final Office Action dated Nov. 30, 2015, Amendment dated Sep. 1, 2015, Non-Final Office Action dated Jun. 3, 2015, Response to Restriction Requirement dated Mar. 27, 2015, Requirement for Restriction dated Feb. 3, 2015, Preliminary Amendment dated Dec. 8, 2014, Response to Notice to File Missing Parts dated Dec. 8, 2014, Part 1 of 2.
Prosecution History for U.S. Appl. No. 14/514,964 including: Notice to File Missing Parts dated Nov. 4, 2014, Part 2 of 2, 62 pages.
First Examination Report for Indian Patent Application No. 398/DEL/2005 dated Oct. 6, 2013, 2 pages.
Issue Notification for U.S. Appl. No. 14/514,964 dated Apr. 27, 2016, 1 page.

\* cited by examiner

RECALL DEVICE

CROSS-REFERENCE TO RELATED APPLICATION

The present application is a continuation of and claims priority of U.S. patent application Ser. No. 14/514,964, filed Oct. 15, 2014, now U.S. Pat. No. 9,344,688, which is a continuation of and claims priority of U.S. patent application Ser. No. 10/790,602, filed Mar. 1, 2004, now U.S. Pat. No. 8,886,298, the content of which is hereby incorporated by reference in their entirety.

TECHNICAL FIELD

The invention relates generally to electronic devices, and more particularly to a recall device.

BACKGROUND

An ability to recall events, personal parameters, and environmental parameters experienced by an individual has many applications. For example, a memory-impaired individual, such as a victim of Alzheimer's Disease, and his/her caregiver can reconstruct a portion of the individual's daily activity to assist in filling in gaps in the individual's memory (e.g., to determine where the individual put their house keys, to identify people with whom the individual interacted, etc.). In another application, the events and parameters associated with a traumatic event, such as an elderly person's fall resulting in injury, etc., may be reconstructed by physicians to better understand the cause and extent of the injuries. Likewise, recalling events and parameters experienced by a child through the day can help a parent or teacher diagnose the child's behavior problems.

However, existing approaches for monitoring such events and parameters do not lend themselves to application in an unobtrusive, wearable device. Such approaches include surveillance cameras and microphones in a room or defined area, and bulky, video cameras and other monitoring devices that are not realistically intended for comfortable, personal use for long periods of time (e.g., all day use) because of their size, storage limitations, power limitations, and other limitations.

SUMMARY

Implementations described and claimed herein address the foregoing problems by providing a small wearable recall device to capture images triggered by a combination of a detection of a capture condition (e.g., changes in motion, temperature or light level) followed by a relatively stable period, as detected by an accelerometer. By triggering on the combination of a detected capture condition followed by a detected stability condition, a clearer image of the environment of an interesting event is expected to be captured. The small size of the recall device makes it possible to integrate it into common portable consumer products, such as MP3 players, purses, clothing, hats, backpacks, necklaces, spectacles, watches, bracelets, collars, and other human-wearable products.

In some implementations, articles of manufacture are provided as computer program products. One implementation of a computer program product provides a computer program storage medium readable by a computer system and encoding a computer program. Another implementation of a computer program product may be provided in a computer data signal embodied in a carrier wave by a computing system and encoding the computer program.

The computer program product encodes a computer program for executing a computer process on a computer system. Acceleration of a camera along at least one axis is monitored using an accelerometer. A capture condition experienced by the camera is detected. A stable condition is detected by the at least one accelerometer along the at least one axis, responsive to the operation of detecting the capture condition. Capture of an image by the camera is triggered based on detection of the capture condition followed by detection of the stable condition.

In another implementation, a method is provided. Acceleration of a camera along at least one axis is monitored using an accelerometer. A capture condition experienced by the camera is detected. A stable condition is detected by the at least one accelerometer along the at least one axis, responsive to the operation of detecting the capture condition. Capture of an image by the camera is triggered based on detection of the capture condition followed by detection of the stable condition.

In yet another implementation, a portable recall device is provided to be carried by a wearer. The portable recall device includes a camera and at least one accelerometer operably connected to the camera. The accelerometer triggering capture of an image by the camera based on detection of a capture condition followed by detection of a stable condition by the at least one accelerometer.

Other implementations are also described and recited herein.

DETAILED DESCRIPTION

Figure 1:
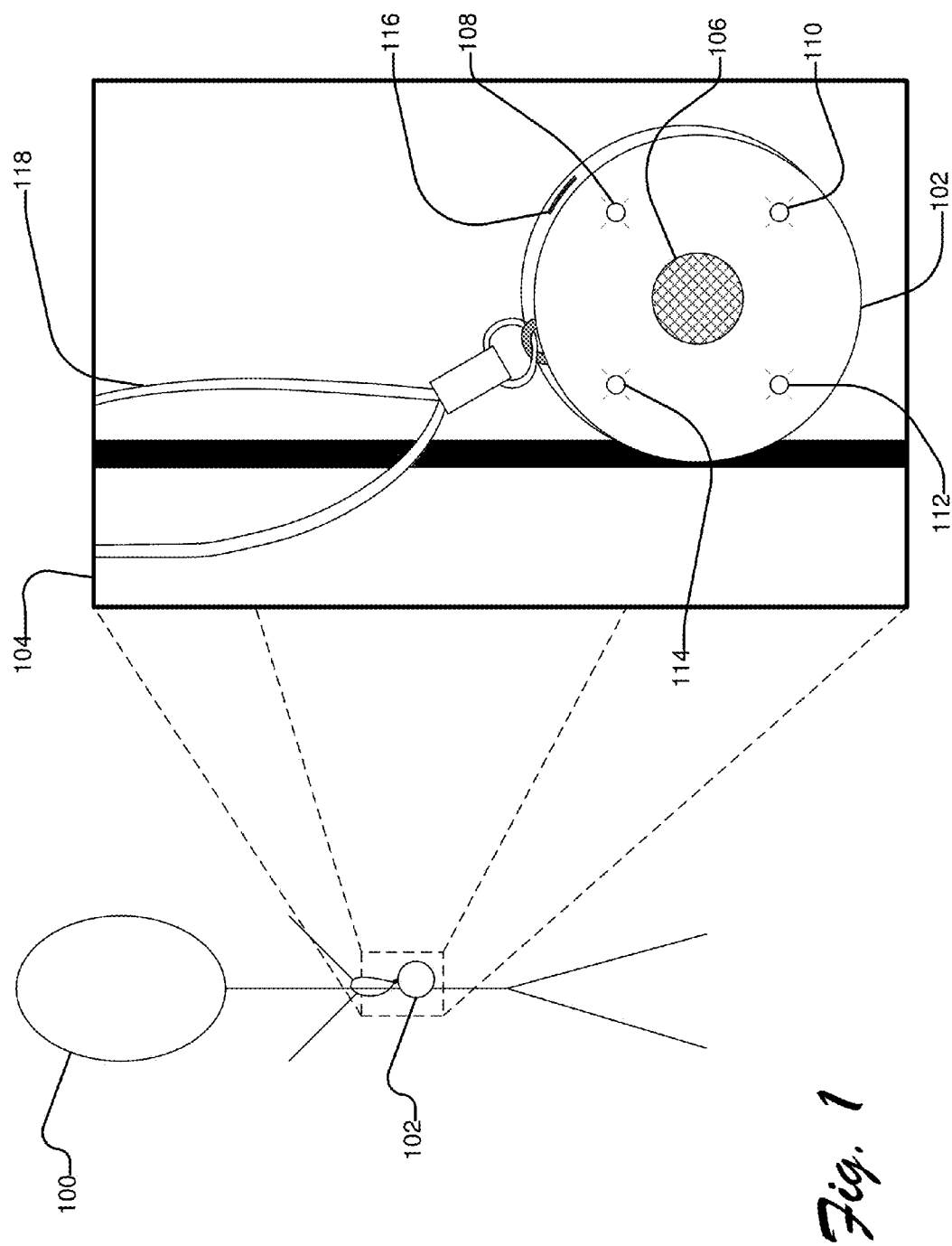
FIG. 1 illustrates an exemplary human-wearable recall device.

FIG. 1 illustrates an exemplary human-wearable recall device. A wearer 100 is shown wearing a recall device 102 on a necklace. It should be understood, however, that a wearer need not be human, but that animals, vehicles, and other objects may wear a recall device for the purpose of selectively recording monitored environmental conditions.

An exploded view of the recall device 102 is shown in box 104. A camera 106, which may include a fish-eye lens, a wide angle lens, or any other kind of lens, is positioned in the center of the recall device 102, although the camera 106 may be positioned at other locations in the recall device 102.

Four light emitting diodes (LEDs) are shown on the face of the recall device 102. LED 108 signals detection of an audio capture condition, such as an increase in detected audio level over a given threshold or a substantial change in average audio level within a given period. LED 110 signals detection of a motion capture condition, such as a detected change of angle of greater than a threshold (e.g., 20°). LED 112 signals detection of a light level capture condition, such as a substantial change in average light level within a given period or an increase in detected light level over a given threshold. LED 114 signals detection of a temperature capture condition, such as an increase in detected ambient temperature level over a given threshold or a substantial change in ambient temperature level within a given period. Other capture conditions than those listed above may alternatively be employed.

A serial port 116 is shown in the recall device 102 to download data monitored by the recall device 102 to a computer system. Recorded data from various in the recall device 102 is saved into memory in the recall device 102. Such data may also be downloaded via the serial port 116 to a more substantial computer system, such as a desktop computer, for subsequent analysis (e.g., using a Microsoft EXCEL spreadsheet application or other analysis tools). Internal settings, such as condition parameters, time settings, etc., may also be uploaded to the recall device 102 via the serial port.

A wireless transceiver (not shown) is coupled to an antenna running up the cord 118. The wireless transceiver may be used to upload and download data as well as to interface with wireless networking protocols, such as Wi-Fi and Bluetooth, and to detect radio frequency signals.

Figure 2:
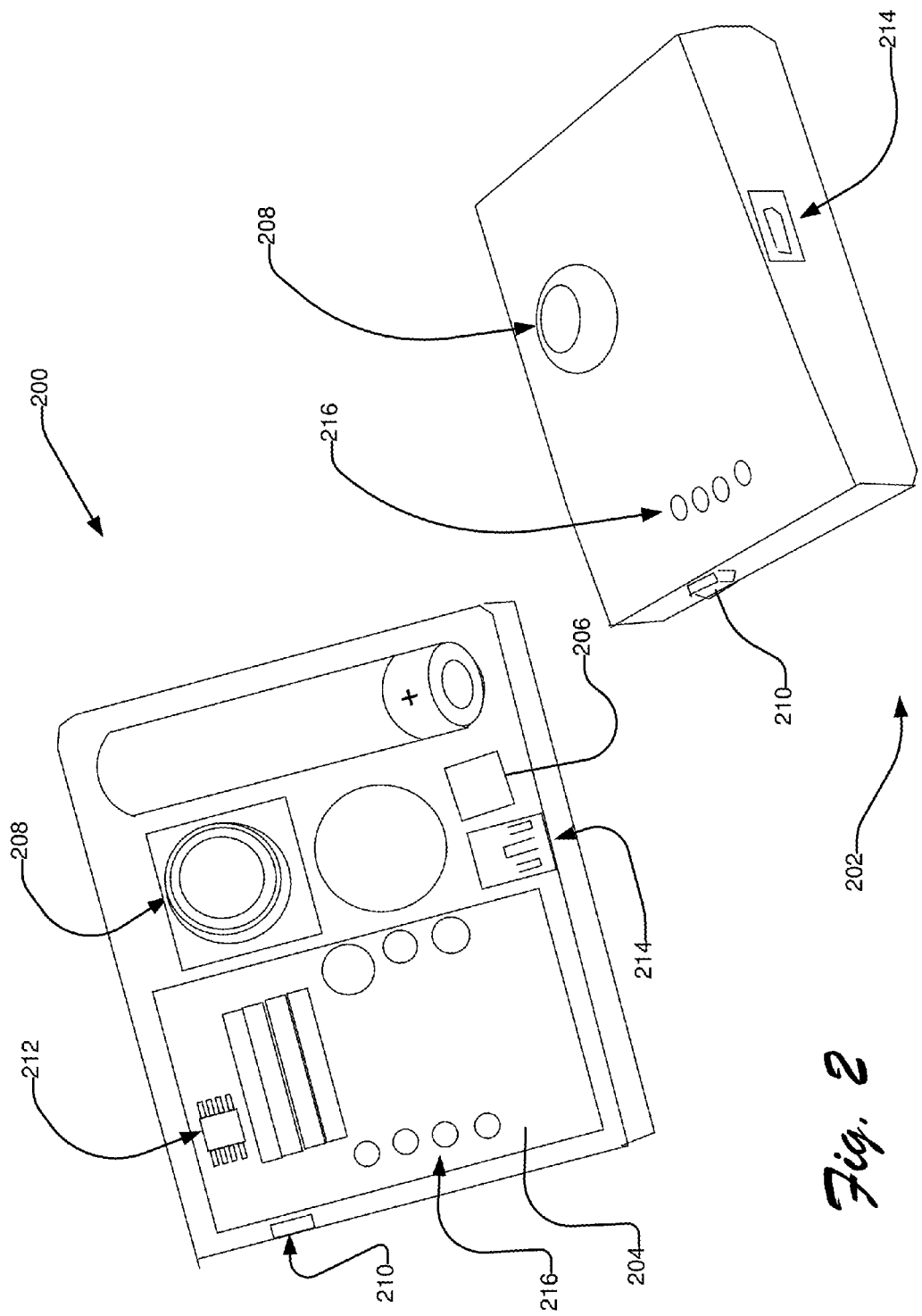
FIG. 2 illustrates an internal plan view and an external perspective view of an exemplary recall device.

FIG. 2 illustrates an internal plan view 200 and an external perspective view 202 of an exemplary recall device. Specific components of exemplary recall devices are described herein; however, it should be understood that other components may be employed in other implementations of a recall device. A microcontroller (not shown) is mounted to the underside of the printed circuit (PC) board 204. In one implementation, a Microchip 20 Mhz PIC16F876 microcontroller is used. A camera 206 and lens 208 are operably connected to the PC board 204 of the recall device. In one implementation, a 50 mm×30 mm×14 mm Sipix Snap 300 kpixel camera module with an additional f2, f2.2, mm lens from Edmunds Optics is employed. In an alternative configuration, a Philips Key008 Camera is employed with an added 2.9 mm lens from Edmunds Optics. An interface to the shutter and mode controls of the camera are provided by reed relays, although other switching elements, such as optical MOSFET transistors, may alternatively be employed.

An accelerometer 210 is mounted to the PC board 204. In the illustrated implementation, a single dual axis +/−10 g ADXL210 accelerometer from Analog Devices is employed. In alterative implementations, multiple multi-axis or single axis accelerometers may be employed. For example, individual single axis accelerometers may be configured to detect acceleration in each of three axes (X, Y, and Z). In an alternative implementation, the 3 axes are designated as roll, pitch and yaw, and a gyroscope is used to detect yaw (rotational acceleration).

A light level sensor 212 mounted to the PC board 204. In one implementation, a digital ambient light level sensor from TAOS, Inc., such as the TCS230, is employed to detect magnitudes of and changes in ambient light levels in experienced by the recall device and, therefore, by the wearer. A change in ambient light level represents an exemplary capture condition that can indicate movement of the wearer from one room to another or from inside to outside. In addition, a change in ambient light level may be imitated by a gesture, such as waving one's hand across the recall device to create a shadow on the light level sensor. As such, an image capture may be triggered by the wearer's gestures without requiring the wearer to actually touching a trigger switch on the recall device. In one such implementation, the delay between detection of the capture event and the triggering of the image capture is prolonged at least as long as a predefined delay period in order to allow proper aiming of the camera at a target.

An ambient temperature sensor (not shown) is mounted to the PC board 204. In one implementation, a National Semiconductor LM75 sensor is employed to detect magnitudes and changes in ambient temperature levels experienced by the recall device. A change in ambient light level represents an exemplary capture condition that can indicate, for example, movement of the wearer from inside to outside.

A serial bus port 214 is mounted to the PC board 204. In one implementation, a universal serial bus interface is employed, although other serial ports, such as an RS-232 interface or IRDA interface, or any other data port, may be employed. The serial bus port (or other interface) may be used to upload and download data to/from the recall device. LEDs 216 indicate detection of various capture events, as discussed with regard to FIG. 1.

Figure 3:
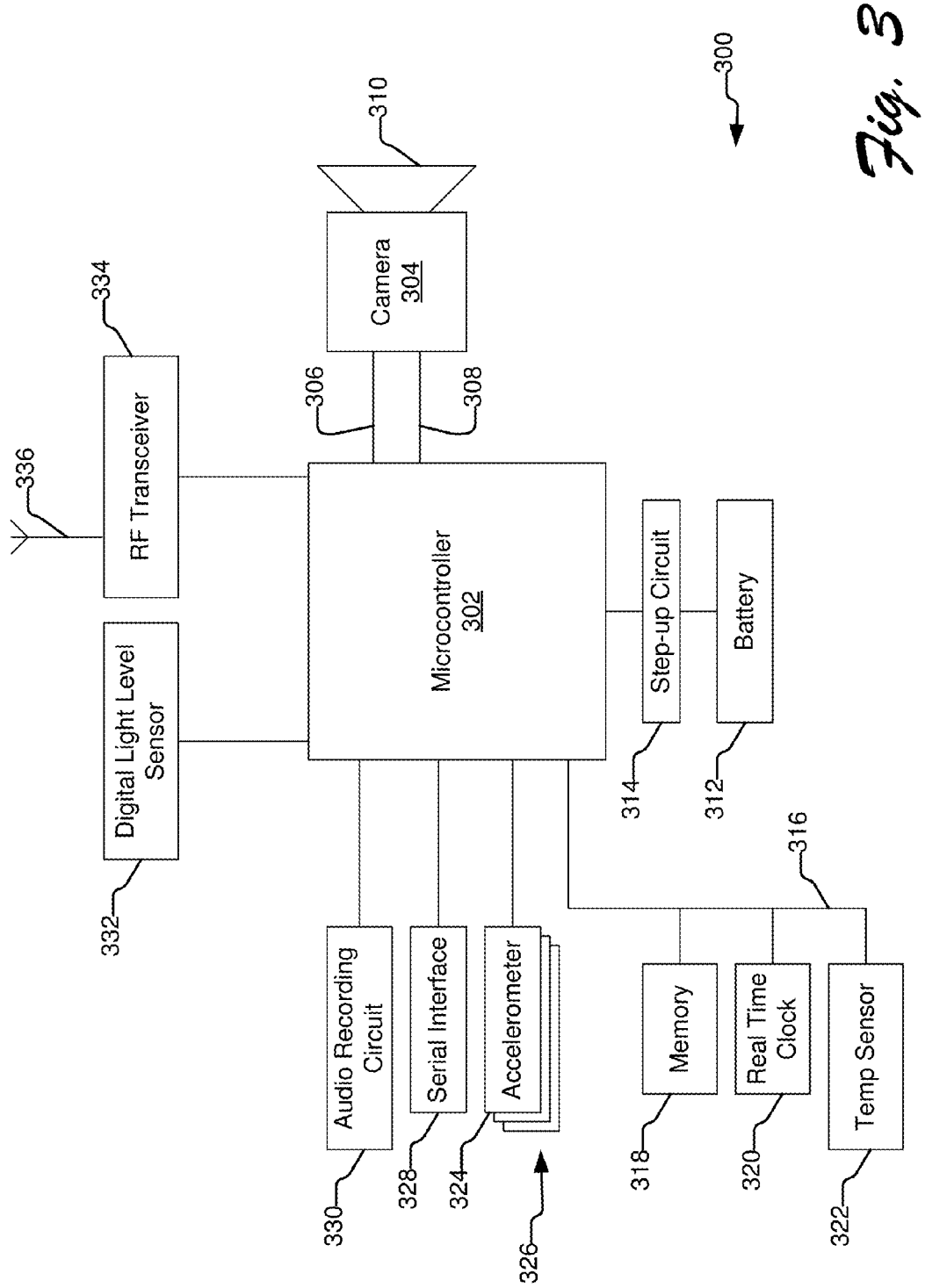
FIG. 3 illustrates a schematic of an exemplary recall device.

FIG. 3 illustrates a schematic of components 300 in an exemplary recall device. A microcontroller 302 is coupled to control a camera 304 using a shutter control line 306 and a mode control line 308. A signal issued by the microcontroller 302 on the shutter control line 306 triggers an image capture in the camera 304. A signal issued by the microcontroller 302 on the mode control line 308 sets the camera in high resolution mode, low resolution, or triggers an erasure of a captured image. A lens 310, such as a normal lens, a wide angle lens, or a fish eye lens, is connected to the camera 304.

A battery 312, such as a NiMH AA 1.5 volt battery, powers the illustrated recall device, including the camera 304. A step-up circuit 314 increases the voltage provided by the battery 312 to 3.7 volts to power the microcontroller 302 and other components on the PC board.

An $I^2C$ bus 316 connects a memory block 318 to the microcontroller 302. The memory block 318 may be used to store logged sensor data and captured images and sound. In one implementation, two 128 Kbyte FLASH memory chips (Microchip 24LC512) are employed. In an alternative implementation, a larger and possibly removable memory modules, such as an SD or MMC card, can be connected will allow up to 1 Gbyte of storage. A real time clock chip 320 (Dallas/Maxim) and an ambient temperature sensor 322 (National Semiconductor LM75) also connected to the microcontroller 302 by the $I^2C$ bus 316.

At least one accelerometer 324 is connected to the microcontroller 302 to detected changes in location and movement. In the illustrated implementation, three single axis accelerometers 326 are employed, one for each axis (X, Y, and Z). A serial bus interface 328, such as a USB or RS-232 interface, is connected to the microcontroller 302 to allow uploading and downloading of data. An audio recording circuit 330 is also connected to the microcontroller 302 to record ambient sound. In one implementation, the audio recording circuit 330 can record continuously for a period of time, although in other implementations, the audio recording circuit 330 is triggered to record in response to detection of a capture condition. A digital light level sensor 332 is connected to the microcontroller 302 to detect light level capture conditions. An RF transceiver 334 and an antenna 336 are connected to the microcontroller to provide or detect Wi-Fi signal communications, to detect RFID transponders, and/or to detect RF signals. In one implementation, a 433 MHz transceiver is employed. In another implementation, a 2.4 GHz radio receiver is employed to detect wireless networks. If the recall device is brought into proximity of a computer having wireless communication capabilities, the recall device can access and transfer images, audio, and other sensor data to the computer (e.g., using Bluetooth or Wi-Fi). As such, a remote computer system can be used to provide device settings, such as camera settings, sensor settings, time settings, etc.

Another user interface mode may be employed in a recall device having a no capacity or limited capacity for switches, buttons, etc. To enable transmission of captured and logged data to a computer system without requiring switches, the camera may be set in a predefined position (e.g., face-down on a table). On power up, one or more accelerometers that detect the predefined position can trigger an automatic download of data to a computer over a wireless network link without any user intervention.

Other exemplary input components that may be employed for monitoring and logging sensor data, including without limitation a Global Positioning System (GPS) transceiver (e.g., a GPS transceiver from Garmin Geko with 10 m resolution and geographic location, altitude, and compass direction detection), a heart rate monitor (e.g., a Polar monitor), a video camera, a gyroscope for detecting rotational conditions (e.g., ADXRS gyroscope from Analog Devices), a chemical sensor (e.g., a Figaro carbon monoxide sensor or a smoke detector), a reverse-biased LED providing a crude optical motion detection based on ambient light changes, and a passive infrared radiation detector (e.g., a Seiko Passive infrared temperature detector) for detecting humans up to 2.5 m from the wearer.

Other exemplary capture conditions may be satisfied by a change in sound level, a change in light level, a change in motion (e.g., as detected by an accelerometer or gyroscope), a change in heart rate, a change in ambient temperature or the wear's body temperature, a change in chemical composition of local environment (e.g., air), detection of a Wi-Fi signal, detection of an RFID transponder, or expiration of a real time clock period.

The various combinations of these components may be used to selectively capture ambient sound and images based on detection of a potentially interesting condition, marked by detection of a capture condition. In this manner, the selective image and sound capture make more efficient use of storage resources by avoiding continuous capture of uninteresting conditions.

Figure 4:
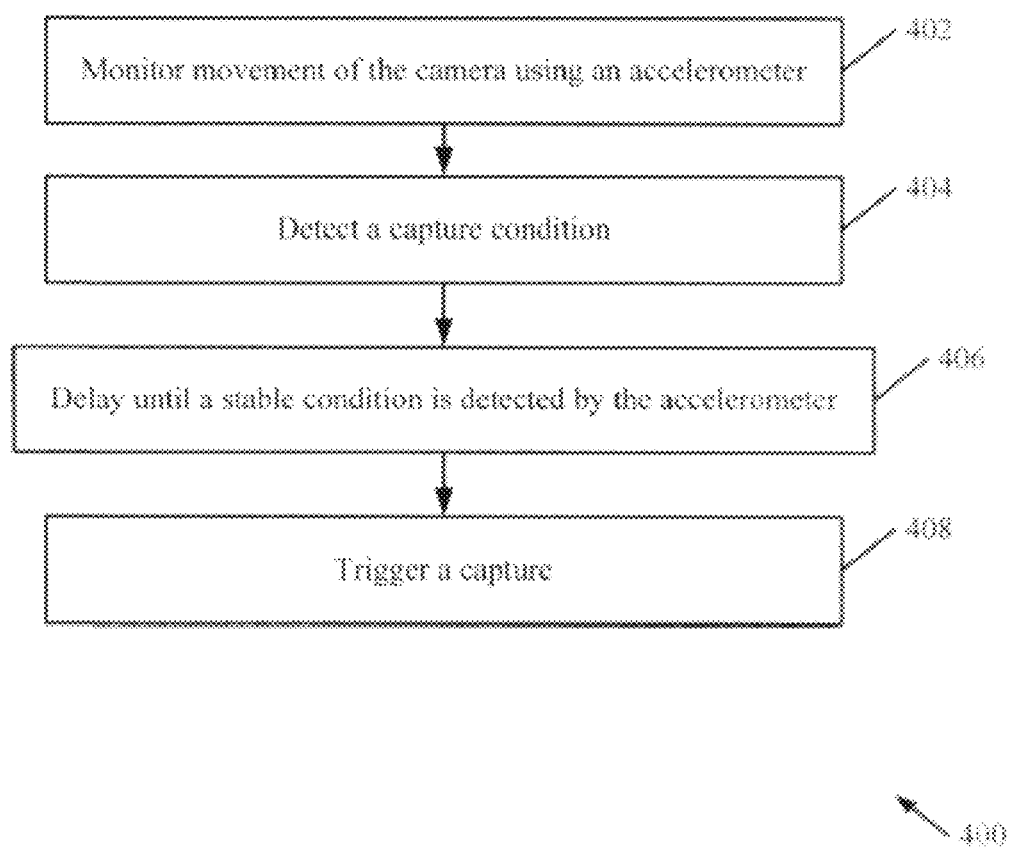
FIG. 4 illustrates exemplary operations of a selective image capture process.

FIG. 4 illustrates exemplary operations 400 of a selective image capture process. A monitoring operation 402 monitors motion of a camera using at least one accelerometer. A detecting operation 404 detects an environmental condition experienced by the camera that is designated as a "capture condition". A capture condition indicates that something that has been previously associated with a potentially interesting environmental event has occurred. For example, if movement from one room to another is deemed to be an interesting environmental event, changes in ambient light level may be deemed to indicate that the wearer has moved to a different room.

In one implementation, an exemplary detecting operation includes the following steps described in pseudocode:
  Detect_light_level:
  (1) Read ambient light level in Lux using TCS230 in current monitoring interval
  (2) Compare current light level reading with the light level reading from previous monitoring interval (e.g., 1 second ago)
  (3) If current reading <50% of previous reading or current reading >200% of previous reading, then indicate capture condition
  (4) Goto Detect_light_level A purpose of detecting the capture condition is to "prime" the triggering of an image capture. However, as the recall device is a wearable device, subject to jitter, the image capture itself is delayed (i.e., managed) until a stable condition is detected by the accelerometer. Therefore, a delay operation 406 delays a trigger operation 408 until a stable condition is detected by the accelerometer(s). In this manner, the quality (e.g., clarity) of the captured image is expected to be better than an image from an unmanaged image capture.

A stable condition is detected when one or more of the accelerometers in the camera detect movement within a predefined range or at or below a predefined threshold. For example, an exemplary recall device may be set to detect a stable condition when all accelerometers sense no movement in their respective axes. However, this setting may severely limit the likelihood of an image capture during periods of otherwise acceptable camera movement, such as when the wearer is standing nearly still. Accordingly, the stable condition may be set to less than a threshold degree change in angle (e.g., 20°) of any given accelerometer output during a measurement period (e.g., 1 second).

In one implementation, an exemplary delay operation includes the following steps described in pseudocode:
  Capture_image:
  (5) Read tilt angle(s) of accelerometer(s) in current monitoring interval
  (6) Compare tilt angle(s) with tilt angle(s) from previous monitoring interval (e.g., 1 second ago)
  (7) If any tilt angle difference exceed 20 degrees, goto Capture_image
  (8) Trigger image capture in camera
  (9) Return After detection of the stable condition, a triggering operation 408 triggers an image capture through the camera module. In alternative implementations, other environmental states may also be captured, including without limitation an audio recording for a given period of time, a GPS reading, a real time clock reading, etc. A purpose of the capture events is to establish a snapshot of the environment as it existed in the temporal proximity of a capture condition. Thereafter, the captured data may be downloaded to a computer system to facilitate reconstruction of the environmental conditions associated with a potentially relevant event.

In another implementation, image capture (including video capture) may occur continuously or periodically, even in the absence of a previous capture condition. For example, the recall device detects a stable condition and triggers an image capture to memory. Thereafter, a temporally proximate capture condition is detected so the captured image is maintained in association with the subsequent capture condition. If no temporally proximate capture condition is detected, the captured image may be deleted from memory to manage storage space. In this manner, the environmental conditions existing just prior to a capture event may be captured and efficiently recorded. A similar algorithm may be applied to audio recordings and other sensory data.

Figure 5:
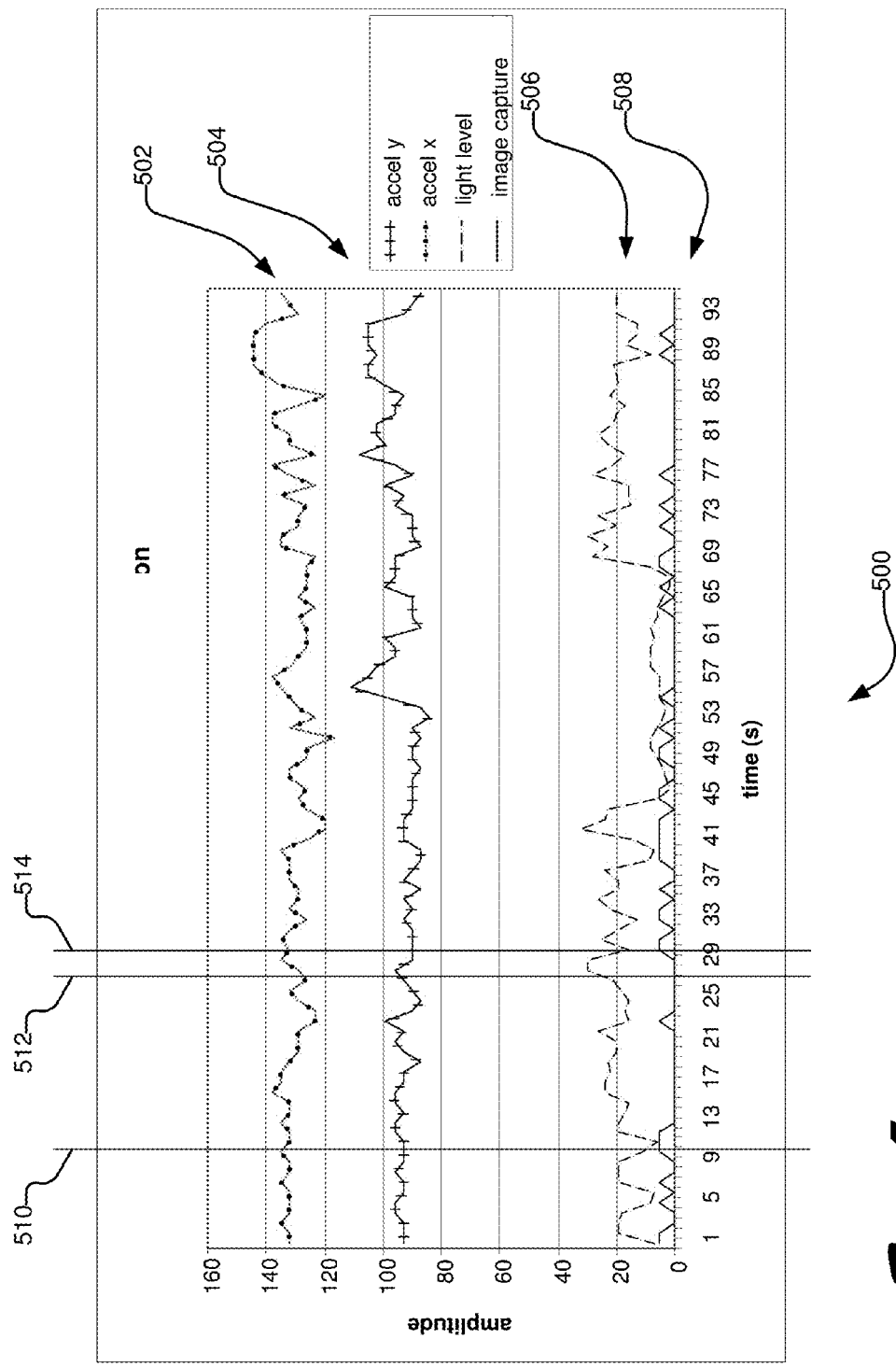
FIG. 5 illustrates exemplary sensor readings relative to image capture events.

FIG. 5 illustrates exemplary sensor readings 500 relative to image capture events. Data 502 indicates readings of an accelerometer associated with the X axis over time. Data 504 indicates readings of an accelerometer associated with the Y axis over time. (Accelerometer readings in the chart correspond to an angle. For example, in one implementation, an accelerometer signal with amplitude 0 represents 0 degrees, an accelerometer signal with amplitude 90 represents 90 degrees, etc.) Data 506 indicates readings of an ambient light level sensor. Data 508 indicates image captures triggered by detection of a capture condition followed by detection of a stable condition.

As shown at time 510, a capture condition has been detected based on the dramatic change in the light level data 506 followed by detection of a stable condition, as indicated by both data 502 and 504. In contrast, at time 512, a dramatic change in light level data 506 represents a capture condition, but an image capture is delayed until time 514, when the stable condition is detected with regard to both data 502 and 504. By managing captures in this manner, images are selectively captured based on detection of a potentially interesting event coupled with a stable period.

Figure 6:
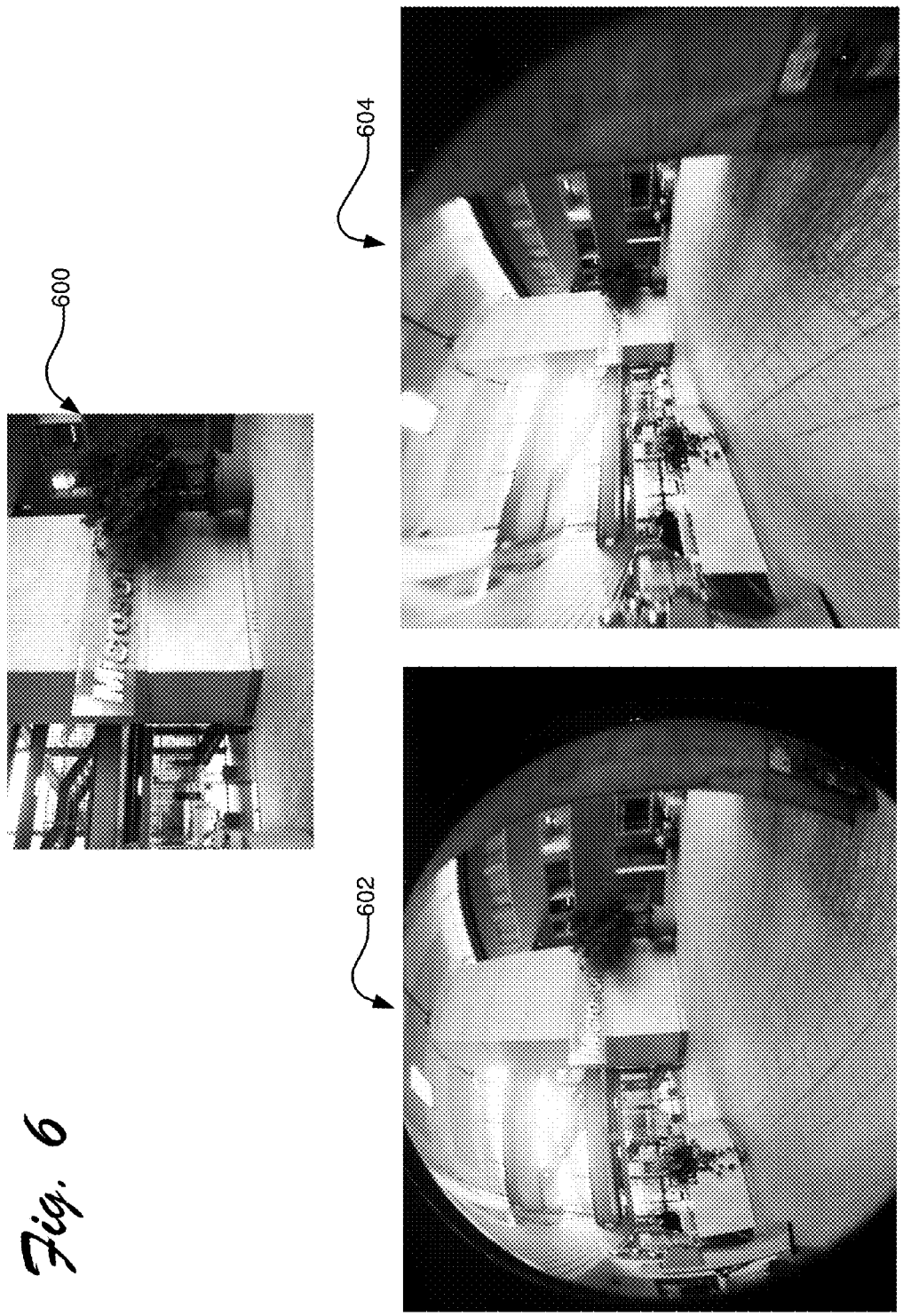
FIG. 6 illustrates an image captured through a normal lens, an image captured through a fish-eye lens, and a corrected version of the captured image.

FIG. 6 illustrates an image 600 captured through a normal lens, an image 602 captured through a fish-eye lens, and a corrected version 604 of the fish-eye image. Using commercially available image editing software, an image captured through the fish-eye lens may be corrected to remove the radial distortion introduced by the fish-eye lens. Coupling the fish-eye image capture with the correction software allows a wearer to capture a maximum amount of environment in an image and to later remove the radial distortion to obtain a relatively normal image. As such, the use of a fish-eye lens is particularly suited to a recall device which captures images with relatively random alignment with the environment.

It should be understood that a variety of data can be logged and downloaded to a computer system for post-processing and/or analysis in order to reconstruct events in the wearer's recent experience. Exemplary outputs of the recall device may include without limitation a continuous audio log; a sequence of audio snapshots; a sequence of image snapshots; a sequence of GPS location, altitude, and direction readings; a motion log; an ambient temperature log; a heart rate log; an RFID detection log; and a wireless network detection log.

Furthermore, in applications intended to facilitate memory recall, a technique referred to as "Rapid Serial Visual Presentation" or RSVP may be employed. RSVP represents the electronic equivalent of riffling a book in order to assess its content, as described in "Rapid Serial Visual Presentation: A space-time trade-off in information presentation", Oscar de Bruijn and Robert Spence, http://www.iis.ee.ic.ac.uk/~o.debruijn/avi2000.pdf, May 2000. Using this technique, a user interface, such as on the recall device or on a client computer system to which the captured data is downloaded, can rapidly display the images in the sequence in which they were captured, under direct user control of various factors, including without limitation speed, direction, and the number of simultaneously visible images. Such display may be combined with temporally synchronized audio captured by the recall device or other logged data.

Manufacturers have not put GPS features in small portable digital cameras at present due to high battery drain. The ADXL210 accelerometer use about 1/130th of the power of a GPS transceiver when operating (typically, 0.6 mA) and, therefore, may be used as an efficient power management component. In one implementation, an accelerometer may be used as a power management component for the GPS receiver. As GPS receiver integrated circuits generally use much current (e.g. 80 mA), the batteries powering the system can be drained easily. By periodically sampling the motion read by the accelerometer (e.g., every second or so), the GPS can be switched off if there is no movement because no change in GPS location has occurred. When movement is detected by the low power accelerometer, the GPS system can be switched back on. A similar power management mechanism can be used to power off the camera, which also has a high current drain. Other sensor inputs, such as light level sensors, can be used for power saving. For example, a camera need not powered in the presence of total darkness.

The embodiments of the invention described herein are implemented as logical steps in one or more computer systems. The logical operations of the present invention are implemented (1) as a sequence of processor-implemented steps executing in one or more computer systems and (2) as interconnected machine modules within one or more computer systems. The implementation is a matter of choice, dependent on the performance requirements of the computer system implementing the invention. Accordingly, the logical operations making up the embodiments of the invention described herein are referred to variously as operations, steps, objects, or modules.

The above specification, examples and data provide a complete description of the structure and use of exemplary embodiments of the invention. Since many embodiments of the invention can be made without departing from the spirit and scope of the invention, the invention resides in the claims hereinafter appended.

What is claimed is:

1. A device comprising:
   an optical image capture component configured to optically capture an image;
   one or more sensors; and
   a controller configured to:
      receive a first signal from at least one of the sensors, the first signal being indicative of movement of the device;
      based on the first signal, detect occurrence of a capture condition indicating a change in motion of the device;
      receive a second signal from at least one of the sensors, the second signal being indicative of movement of the device;
      based on the second signal, detect occurrence of a stable condition;
      determine that the stable condition and the capture condition occurred within a predefined time period of one another; and
      based on the determination that the stable condition and the capture condition occurred within the predefined time period, control the device to obtain the image in a data storage component associated with the device, wherein
         the stable condition occurs before the capture condition,
         the image is captured by the image capture component before the determination, and
         the controller is configured to control the device to obtain the image by controlling storage of the image in the data storage component based on the determination.

2. The device of claim 1, wherein the device comprises a portable computing device and the optical image capture component comprises a camera on the portable computing device.

3. The device of claim 1, wherein the image comprises an image in a video sequence.

4. The device of claim 1, wherein the controller is configured to:
  detect the capture condition based on a determination that acceleration of the device is above a threshold; and
  detect the stable condition based on a determination that acceleration of the device is below a threshold.

5. The device of claim 1, wherein the controller is operably coupled to the optical image capture component and configured to control the device to obtain the image by sending a trigger signal to the optical image capture component, the trigger signal triggering the optical image capture component to capture the image.

6. The device of claim 5, wherein the capture image is stored in a data storage component that is local to the device.

7. The device of claim 1, wherein the predefined time period comprises a predefined time period after the capture of the image.

8. The device of claim 7, wherein the controller is configured to control the storage of the image by deleting the image from the data storage component if the capture condition is not detected in the predefined time period after the capture of the image.

9. The device of claim 1, wherein the controller is operably coupled to the image capture component and configured to trigger the image capture component to capture the image based on the detection of the stable condition.

10. The device of claim 9, wherein the controller is configured to:
  receive the captured image from the optical image capture component; and
  maintain storage of the image in the data storage component based on the determination that the stable condition and the capture condition occurred within the predefined time period.

11. The device of claim 1, and further comprising:
  an environmental sensor configured to generate an environmental condition signal indicative of an environmental condition in an environment of the device, and wherein the controller is configured to receive the environmental condition signal and to detect the capture condition based on both the environmental condition and the first signal.

12. The device of claim 11, wherein the environmental condition comprises at least one of:
  a change in ambient sound;
  a change in ambient temperature;
  a change in a user's heart rate;
  a change in light level; or
  a change in infrared radiation.

13. The device of claim 11, wherein the environmental sensor comprises a chemical sensor.

14. The device of claim 11, and further comprising:
  a plurality of environmental sensors configured to generate environmental condition signals indicative of a plurality of different types of environmental conditions in an environment of the device, each environmental sensor corresponding to a different one of the types of environmental conditions; and
  a plurality of visual indicators, each corresponding to a different one of the environmental sensors;
  wherein the controller is configured to:
    receive an environmental condition signal from a particular one of the environmental sensors;
    detect the capture condition based on the received environmental condition signal; and
    activate the visual indicator corresponding to the particular environmental sensor.

15. A computer-implemented method comprising:
  receiving a first sensor signal indicative of a first acceleration of a portable computing device;
  based on the first acceleration, detecting a capture condition by determining that a change in motion of the portable computing device is above a threshold;
  receiving a second sensor signal indicative of a second acceleration of the portable computing device;
  detecting a stable condition by determining that the second acceleration is below a threshold;
  determining that the stable condition occurred within a defined temporal proximity of the capture condition;
  based on determining that the stable condition occurred within a defined temporal proximity of the capture condition, controlling an image capture component associated with the device to capture an image;
  storing the image in memory local to the portable computing device;
  receiving a third sensor signal indicative of an orientation of the device; and
  based on the orientation of the device, transferring the stored image from the memory to a computing system that is separate from the portable computing device.

16. The computer-implemented method of claim 15, wherein transferring the stored image from the memory comprises transferring the stored image to the computing system over a wireless network link.

17. A device comprising:
  an image capture component configured to capture an image; and
  a controller configured to:
    receive a first sensor signal indicative of a first acceleration of the device;
    detect a stable condition by determining that the first acceleration is below a threshold;
    trigger the image capture component to capture the image;
    receive a second sensor signal indicative of a second acceleration of the device;
    based on the second acceleration, detect a capture condition by determining that a change in motion of the device is above a threshold, wherein the stable condition occurs before the capture condition;
    after the image is captured by the image capture component, determine that the capture condition occurred within a defined temporal proximity of the stable condition; and
    based on determining that the stable condition occurred within a defined temporal proximity of the capture condition, control storage of the image in a data storage component.

18. The device of claim 17, wherein the device comprises a portable computing device, the image capture component comprises a camera on the portable computing device, and the data storage component comprises memory on the portable computing device.

* * * * *